(12) United States Patent
Pettibon

(10) Patent No.: US 7,322,977 B2
(45) Date of Patent: Jan. 29, 2008

(54) SPINAL ADJUSTING DEVICE AND METHOD

(76) Inventor: Burl Pettibon, 89 Raft Island Dr., Gig Harbor, WA (US) 98335

( * ) Notice: Subject to any disclaimer, the term of this patent is extended or adjusted under 35 U.S.C. 154(b) by 211 days.

(21) Appl. No.: 10/317,410

(22) Filed: Dec. 11, 2002

(65) Prior Publication Data

US 2003/0093074 A1    May 15, 2003

Related U.S. Application Data

(63) Continuation-in-part of application No. 09/680,555, filed on Oct. 5, 2000, now abandoned.

(51) Int. Cl.
*A61B 17/56* (2006.01)
*A61F 5/00* (2006.01)

(52) U.S. Cl. .................. 606/53; 606/244

(58) Field of Classification Search .............. 5/600, 5/607, 612, 622, 634, 635, 640, 643; 602/34; 606/237, 240, 244, 245, 243, 53
See application file for complete search history.

(56) References Cited

U.S. PATENT DOCUMENTS

| | | | | |
|---|---|---|---|---|
| 221,587 A | * | 11/1879 | Manwarring | 5/634 |
| 229,286 A | * | 6/1880 | Towers | 5/634 |
| 1,079,795 A | * | 11/1913 | Naysmith | 606/244 |
| 1,281,074 A | * | 10/1918 | Russell | 5/634 |
| 1,336,294 A | * | 4/1920 | Hackman | 5/634 |
| 2,211,453 A | * | 8/1940 | Buttikofer | 5/634 |
| 4,759,769 A | * | 7/1988 | Hedman et al. | 623/17.13 |
| 5,147,287 A | * | 9/1992 | Jewell et al. | 602/32 |
| 5,458,642 A | * | 10/1995 | Beer et al. | 623/17.13 |
| 5,724,970 A | * | 3/1998 | Votruba et al. | 600/415 |
| 6,422,777 B1 | * | 7/2002 | Landrau et al. | 401/266 |

* cited by examiner

*Primary Examiner*—Pedro Philogene
(74) *Attorney, Agent, or Firm*—Seed IP Law Group PLLC

(57) ABSTRACT

A spinal adjusting device having a base plate assembly with an upper plate assembly coupled thereto, the base plate assembly configured to permit the upper plate assembly to drop a predetermined distance when subjected to a predetermined force. The base plate assembly includes a coupling mechanism having a drop assembly that enables adjustment in the amount of predetermined force required to drop the upper plate assembly onto the base plate. A patient is placed with their neck supported at the vertebra adjacent to the vertebra in need of repositioning. The patient's cervical spine and skull are flexed or extended with sufficient force to cause the entire upper assembly to drop, facilitating repositioning of the target vertebrae.

21 Claims, 13 Drawing Sheets

SPINAL ADJUSTING DEVICE AND METHOD

This is a continuation in part application of Ser. No. 09/680,555 filed Oct. 5, 2000 now abandoned.

TECHNICAL FIELD

This invention pertains to the restoration of form and function of the skull on the cervical spine (neck) and, more precisely, relates to adjustment of the backward (extension) as well as the forward and/or lateral (flexion) motions of the skull on the cervical spine (neck).

BACKGROUND OF THE INVENTION

Injuries to the neck, especially flexion and extension (whiplash) injuries, cause joint, ligament, and muscle disfunctions that can limit motions of one or more of the spinal joints. Referring initially to FIGS. 1-4, shown in FIG. 1 is the balanced position of the head 20 with the skull 22 on the lateral upright cervical vertebral column 24. The head 20 is in equilibrium when the eyes 26 look horizontally, as shown by axis A. With the head 20 in this position, the plane of the bite, shown as axis B, is also horizontal, or parallel to axis A. Force is produced by the weight of the head 20 through its center of gravity lying at the front of the sella turcicia, which is shown as the intersection C of the gravity force line D and the horizontal axis A. The gravity force line D extends from the intersection C with the horizontal axis A through the anterior one-third of the C4-C5 disk.

The angle of the normal cervical spine lateral curve is measured between axis lines E of the posterior border of the C2 vertebra and the axis line F off the posterior border of the C7 vertebra. Normally, the intersection of the axis lines E and F should form an acute angle in the range of about 43° to 45°.

Referring to FIG. 2, the skull 22 and the cervical vertebral column 24 normally each have 7.5 degrees of forward flexion and 7.5 degrees of backward extension movement relative to the vertebrae below, producing 130 degrees of total flexion of the skull and neck.

Referring to FIGS. 3 and 4, FIG. 3 shows a representation of an x-ray of an injured skull 26 and cervical spine 28. The center of gravity line D is reproduced to show the displacement of the cervical spine 28 from its normal position. In this case, the cervical spine 28 is displaced from its normal position relative to the center of gravity line D by approximately 1-¼ inch as shown in FIG. 3. There is a need for a device that can help restore the cervical spine 48 to a normal or substantially normal position as shown in FIG. 4.

SUMMARY OF THE INVENTION

The disclosed embodiments of the invention are directed to a spinal adjusting device that includes a base plate assembly and an upper plate assembly, the upper plate assembly connectable to the base plate assembly such that the upper plate assembly will drop to the base plate assembly when subjected to a predetermined amount of force.

In accordance with another embodiment of the invention, the base plate assembly includes a base plate and a coupling mechanism that couples the upper plate assembly to the base plate, the coupling mechanism including a drop assembly.

According to an additional embodiment of the invention, a reset lever is provided, affixed to the base plate of the device and configured to move the upper plate assembly into the cocked, or reset, position when a downward force is applied to a handle of the lever.

In accordance with a method of the present invention, the spinal adjusting device is placed under the patient's neck supporting the vertebra just below the vertebra and/or skull in need of repositioning. The coupling mechanism holds the upper assembly above the base plate until the patient's cervical spine and skull are flexed or extended, as required, with sufficient force to cause the upper assembly to drop to the base plate.

DETAILED DESCRIPTION OF THE INVENTION

Figure 5:
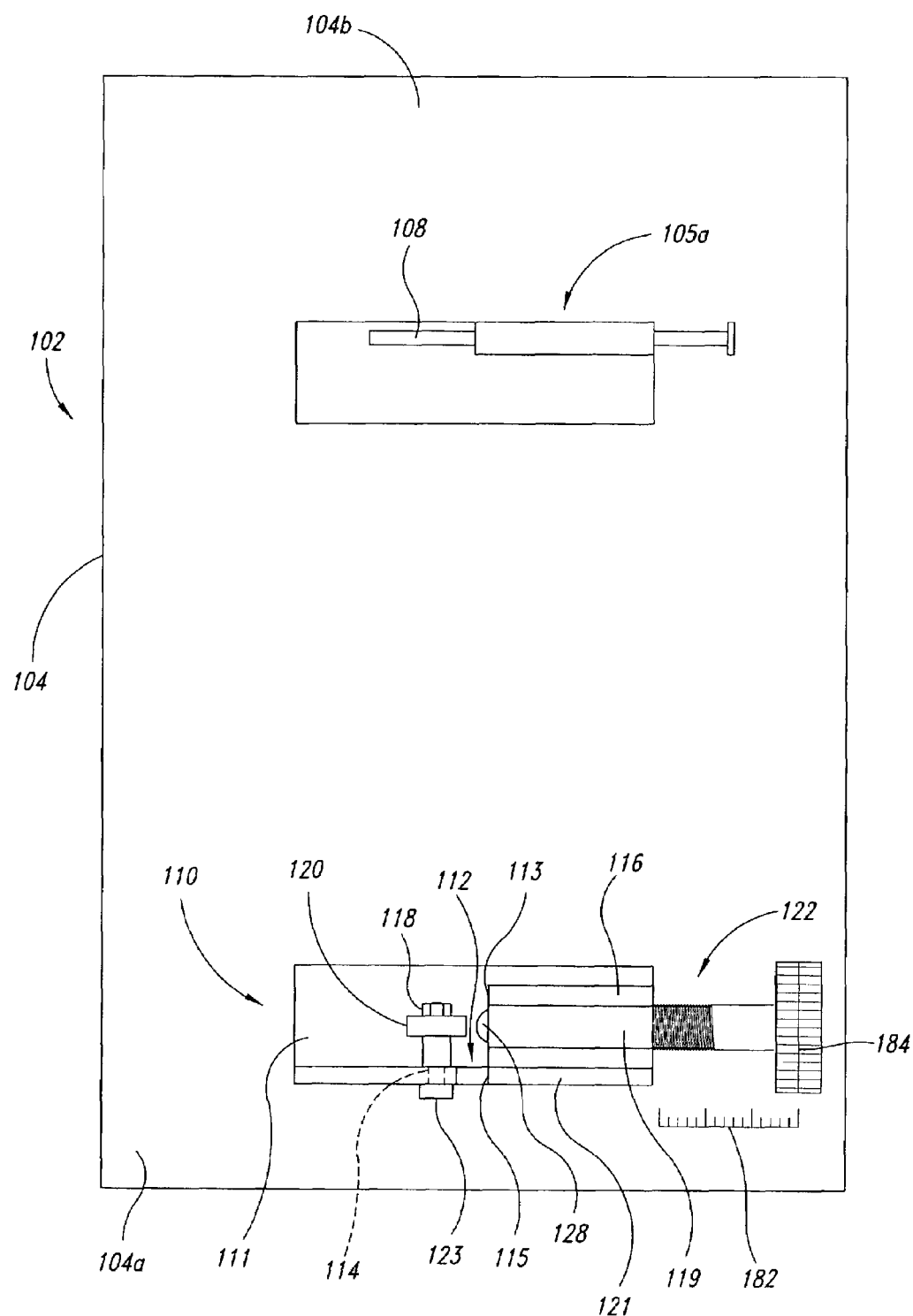
FIG. 5 is a top plan view of a base plate assembly of a device in accordance with an embodiment of the invention.
Figure 6:
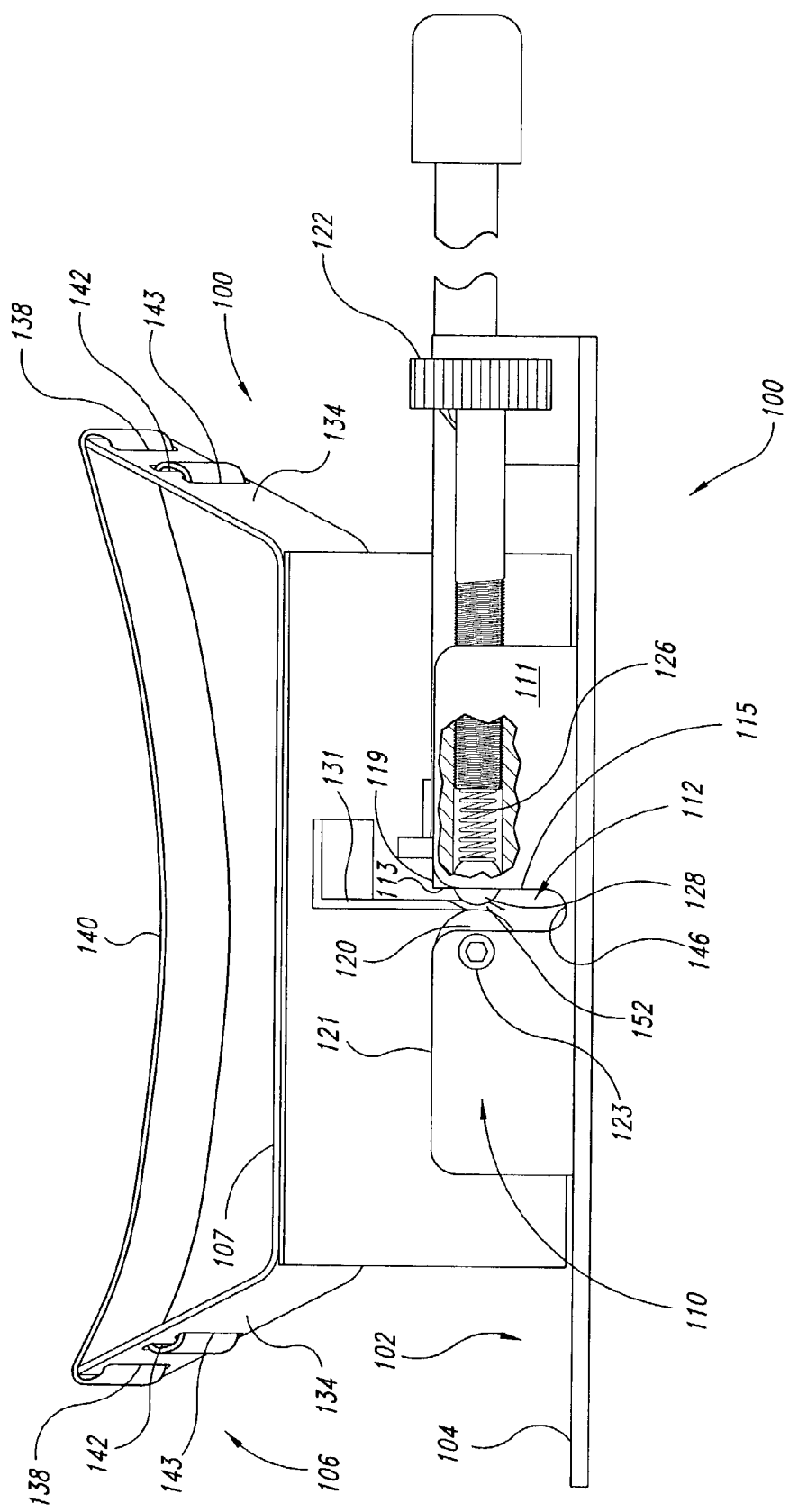
FIG. 6 is a front elevation view of the assembled device of FIG. 5, showing the device in "cocked" position.

Referring initially to FIGS. 5-7B, shown therein is a spinal adjusting device 100, including a base plate assembly 102 (shown in FIG. 5) for use with a patient 103. In FIG. 5 is shown the components of the base plate assembly 102. The base plate assembly 102 includes a base plate 104, ideally made of ⅛th inch steel plate. In one embodiment the base plate 104 has dimensions of 10 inches wide and 12 inches long.

One half 105a of a pin hinge 105 is welded in the center of the base plate 104 for attachment of an upper plate assembly 106 with a pin 108. A tension adjustable drop assembly 110 is welded or otherwise affixed to the center of the forward end 104a of the base plate 104. In one embodiment, the drop assembly 110 is ideally made of a 1½×1½×⅛ inch thick angle plate 111. There is a ½ inch wide slot 112 milled in the center of the upright angle plate 111. There is a ¼ inch hole 114 drilled ½ inch to the right of the slot 112 and ½ inch from the top of the angle plate 111.

There is a 1½ inch long coupling nut 116 welded onto the upright angle plate 111. The edge 113 of the nut 116 is even with the right edge 115 of the milled slot 112. The top 119 of the coupling nut 116 is level with the top 121 of the angle plate 111. A ¼th inch bolt 123 inserts in the hole 114 and attaches a ¾ inch diameter by ½ inch wide roller bearing 120 thereto with a nut 118. A ½ inch diameter thumbscrew 122 3½ inches long is on the right side of the upright angle plate 111. When the thumbscrew is screwed into the coupling nut 116 attached to the plate 111, it compresses a 1 inch long tool spring 126 (shown in the cutaway in FIG. 6) against a ½ inch ball bearing 128. The ball bearing 128 is compressed against roller bearing 120 by the spring 126 and the thumbscrew 122. The amount of tension between the ball bearing 128 and the roller bearing 120 may be adjusted by turning the thumbscrew 122 in or out of the coupling nut 116.

Figure 7:
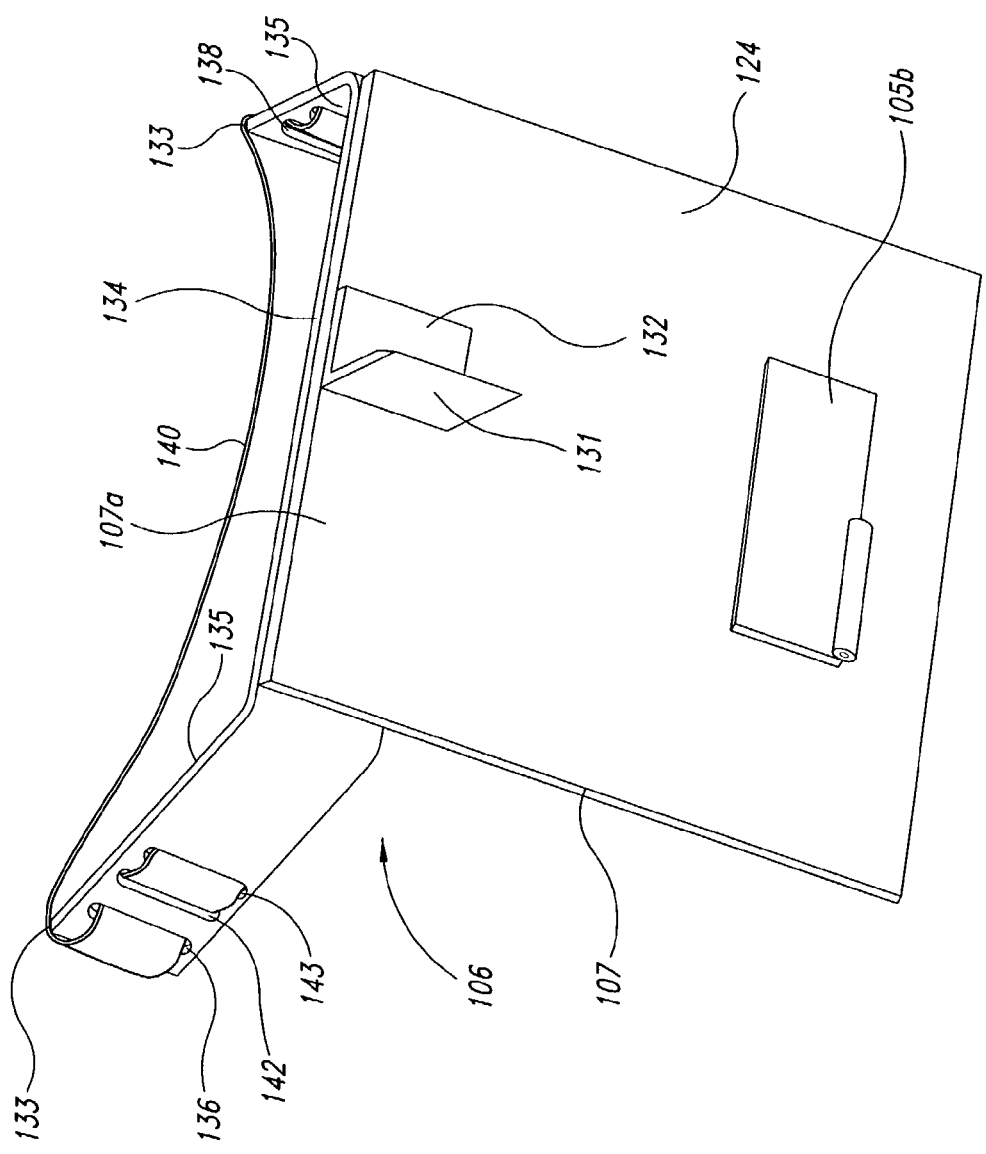
FIG. 7 is an isometric view of an upper plate assembly of the device of FIG. 5.

Shown in FIG. 7 is an upper plate assembly 106. In one embodiment, the assembly 106 includes an upper plate 107 that is 6 inches wide and 8-½ inches long. One half 105b of the pin hinge 105 is welded on the under side 124 of the upper plate 107. This one half hinge 105b fits into the other one half hinge 105a and attaches the upper plate 107 to the base plate 104 when the pin 108 is inserted into pin hinge halves 105a and 105b. A 1½×1½×⅛th inch thick angle bar 132 1 inch long is welded to the center of the front end 107a of the under side of the upper plate 107. The angle bar 132 includes a protruding leg 131 that rests on the laterally compressed bearings 120 and 128 when the invention is in the cocked position (See FIG. 6).

Figure 8:
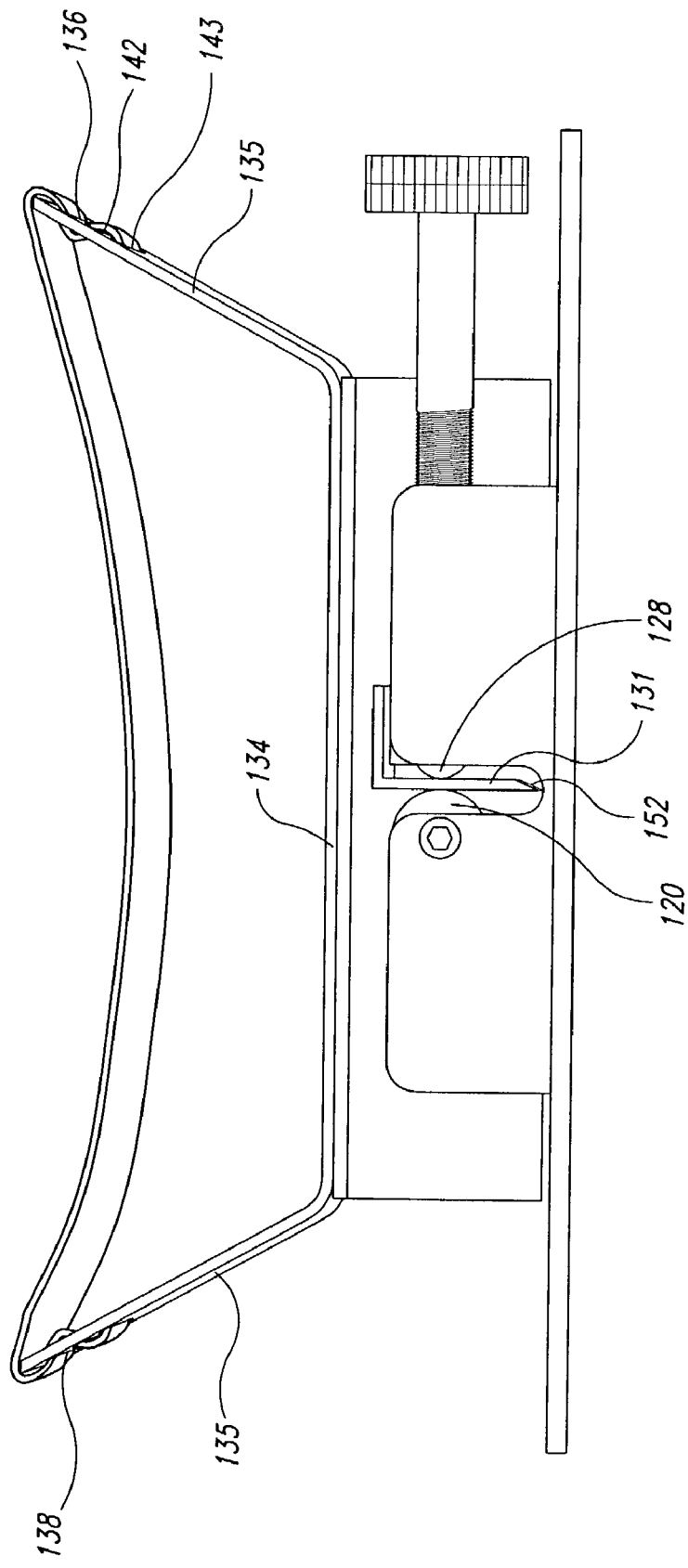
FIG. 8 is a front elevation view of the device of FIG. 6, in "uncocked" position.

To activate the device, sufficient force is applied to the patient's head and neck to cause the compressed bearings 120 and 128 to separate so that the angle bar 132 falls to the bottom 146 of the slot 112 and the entire upper plate 107 drops to the uncocked position, as shown in FIG. 8. The degree of force required to cause the compressed bearings 120 and 128 to separate as described may be referred to as the threshold force.

In the illustrated embodiment, the protruding leg 131 has an angled bottom face 152. In another embodiment, the end face of the protruding leg 131 may have a flat surface to reduce the damage to the bottom plate. In the embodiment illustrated in FIGS. 5-7 the upper plate drops approximately 1½ inches. A bent metal bar 134, having upright legs 135 resembling a goal post, is affixed to the forward edge 107a of the upper surface of the upper plate 107. In one embodiment, the metal bar 134 is ⅛th inch thick and 1½ inches wide. The two ends 133 of the bar 134 are bent upward at about a 62 degree angle to form 5 inch high legs 135 that are 11½ inches apart at the top and 8-12 inches apart at the bottom (see FIG. 8). Two ⅛th inch×1 inch horizontal slots 136 and 138 are milled ⅛th inch from the end 133 in each upright leg 135. The slots 136 and 138 are used for the attachment of a 3/32nd×⅞th inch nylon strap 140, which is, in this embodiment, 16 inches long, between the two upright legs 135. Two additional ⅛th×1 inch long horizontal slots 142, 143 (see FIG. 7) are milled below either slot 136 or slot 138 on one of the upright legs 135 for securing the nylon strap 140 to the upright legs 135.

Figure 9A:
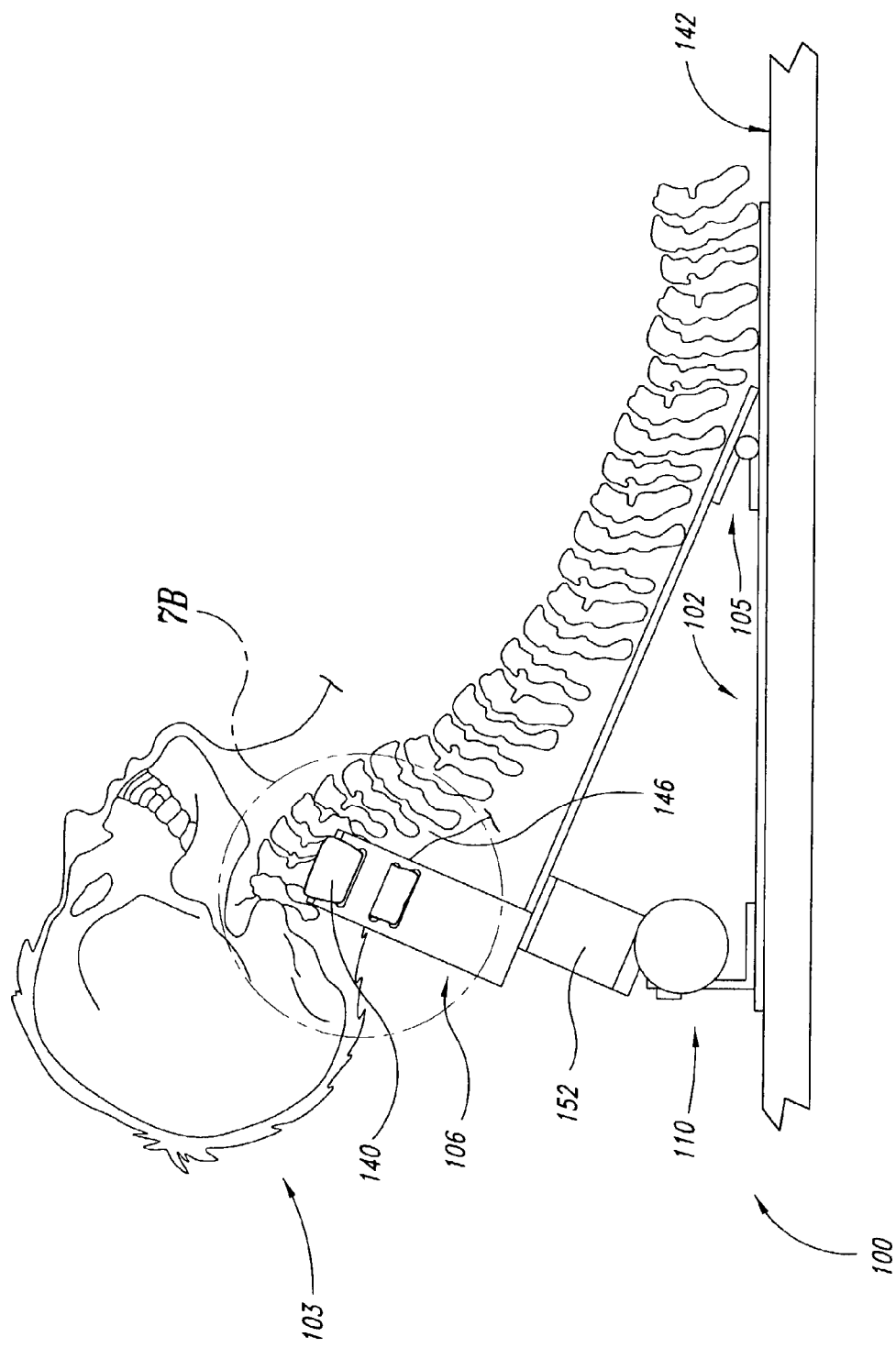
FIG. 9A is an illustration of a cervical vertebral column properly positioned for treatment in accordance with an embodiment of the invention.
Figure 9B:
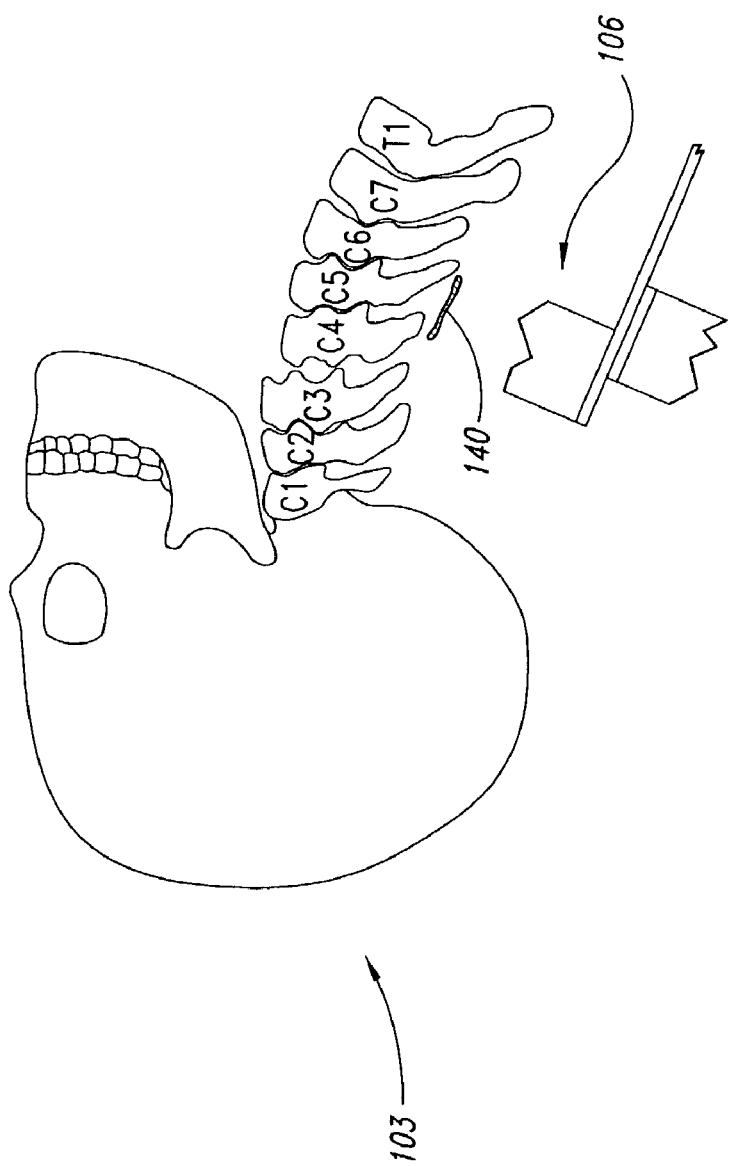
FIG. 9B is a detail of the embodiment of FIG. 9A.
Figure 10A:
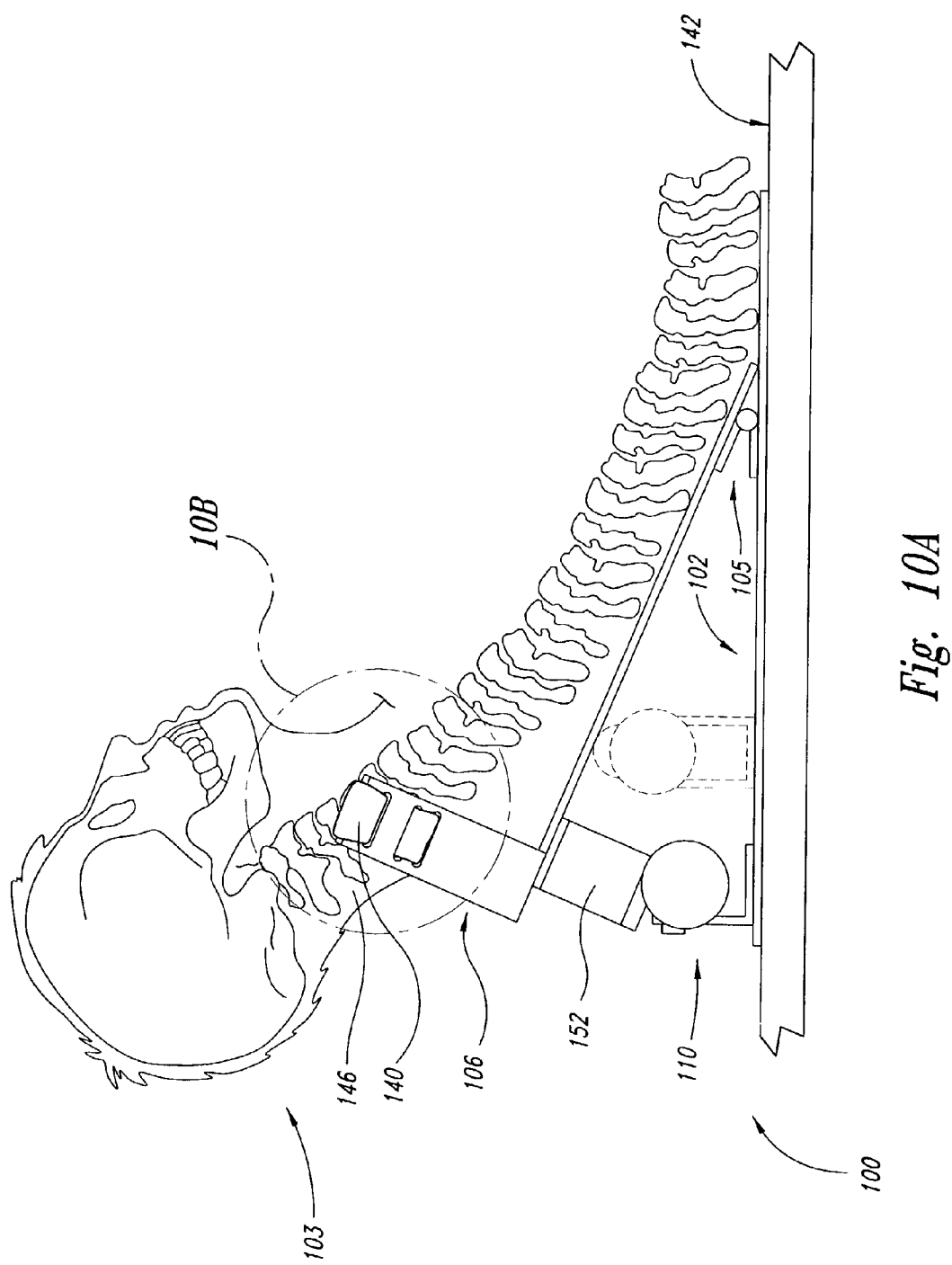
FIG. 10A is an illustration of a cervical vertebral column properly positioned for treatment in accordance with another embodiment of the invention.
Figure 10B:
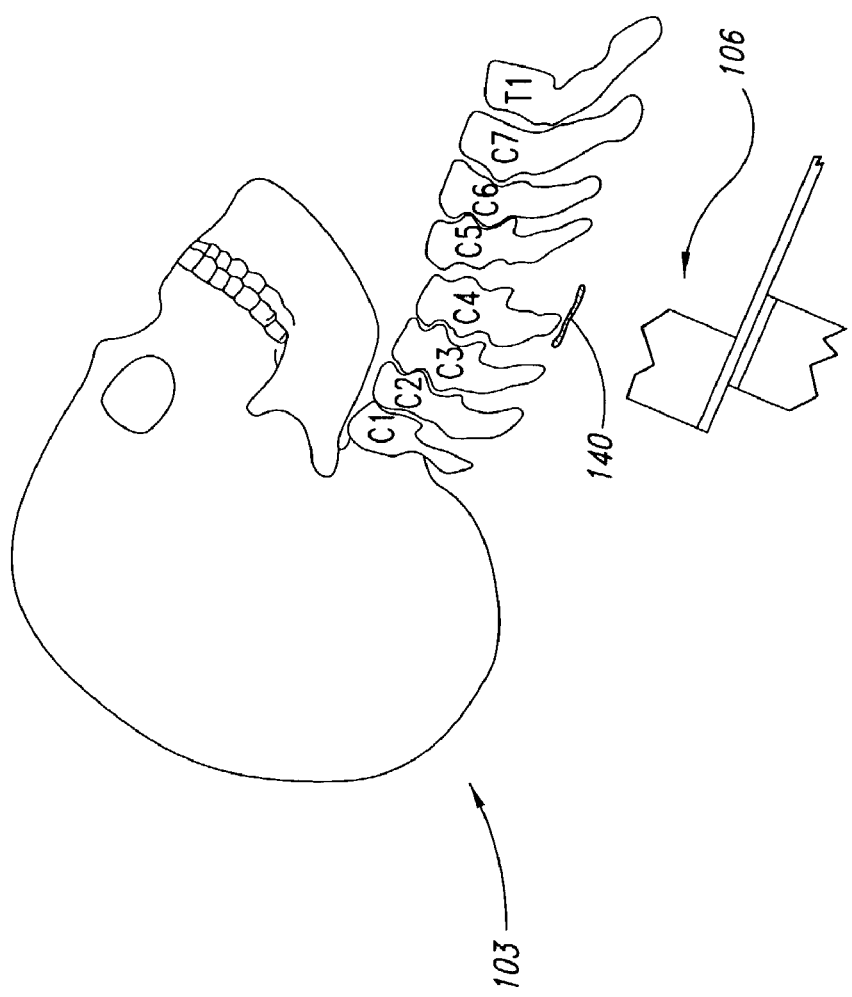
FIG. 10B is a detail of the embodiment of FIG. 10A.

The nylon strap 140 supports the back or sides of the patient's neck and may be precisely positioned under the lower vertebrae of the two vertebrae in need of correction (see FIGS. 9 and 10). In use, the device 100 is preferably placed on a patient table 142. It may be secured to the table 142 with fasteners or releasable connectors (not shown) or it may rest upon the table 142. To use the device 100, the patient 103 is placed supine on the firm table 142. The device 100 is placed under the patient's neck 146 (see FIGS. 9 and 10). The nylon strap 140 is positioned under the vertebra just below the vertebra in need of repositioning for extension, as shown in FIGS. 9A and 9B, or under the vertebra just above the vertebra in need of repositioning for flexion, as in FIGS. 10A and 10B 11. FIG. 9A shows the general arrangement of a patient on the device in a position for extension. FIG. 9B is a detailed view of the skull and cervical vertebrae showing a misalignment between vertebrae C3 and C4. The strap 140 is shown positioned under C4. FIGS. 10A and 10B illustrate a similar configuration, in which the patient is positioned for flexion, with the misalignment between C4 and C5. The strap 140 is again positioned under C4.

The upper assembly 106 is made ready for use by lifting and rotating the upper plate 107 upward about the hinge pin 108 that connects the upper plate 107 and the base plate 104. In this position, the angle bar 132 of the upper plate 107 is resting on the intersection of the compressed bearings 120 and 128 of the adjustable drop assembly 110 on the base plate 104 (see FIGS. 12 and 13).

A skilled practitioner then flexes or extends and/or rotates the patient's entire cervical spine and skull on the nylon strap 140, depending on the action (flexion or extension and/or rotation) that is needed to reposition the involved vertebrae relative to each other and/or the skull relative to the top vertebra.

After the spine 28 has been properly positioned and stressed (see FIGS. 9 and 10), the skilled practitioner then applies an additional amount of force, i.e., the threshold force, on the patient's skull or body in the direction to be stressed, that is, flexed or extended. This additional force must be sufficient to cause the angle bar 132 protruding from the upper plate 107 to overcome the resistance of the compressed bearings 120 and 128, so that the entire upper assembly 106 and the patient's head and neck drop until the protruding leg 131 on the angle bar 132 strikes the bottom 146 of the slot 112.

Figure 1:
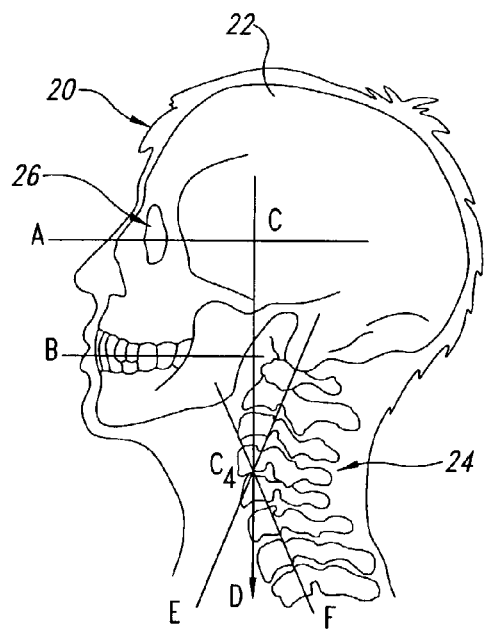
FIG. 1 is a cross-sectional illustration of the skull on the lateral upright cervical vertebral column.
Figure 2:
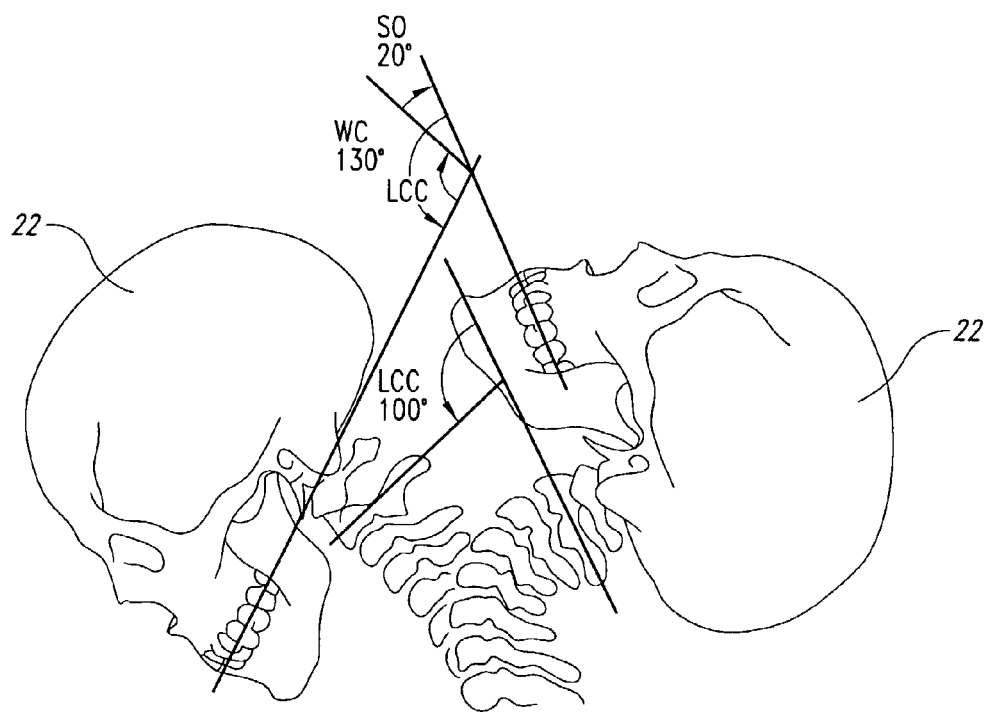
FIG. 2 is an illustration of normal forward flexion and backward extension movement of the skull and cervical vertebrae.
Figure 3:
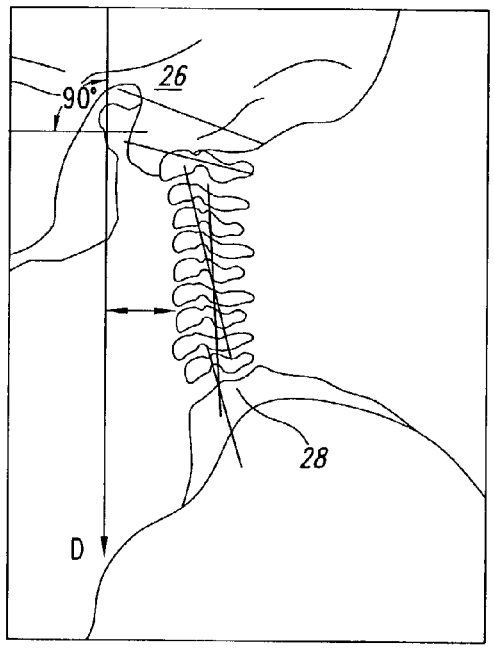
FIG. 3 is from an x-ray of an injured skull and cervical spine before treatment in accordance with the invention.
Figure 4:
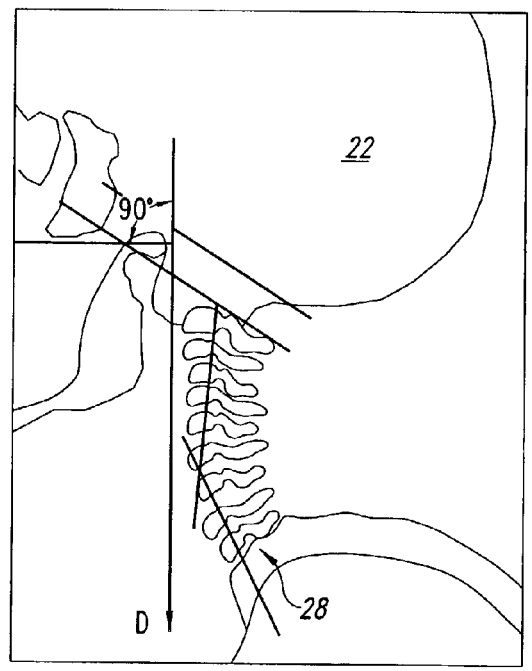
FIG. 4 is from an x-ray of the same skull and cervical spine as in FIG. 3, after treatment in accordance with the invention.

The movement of the angle bar 132, the upper assembly 106 and the vertebra resting on the nylon strap 140 are abruptly stopped when the leg 131 hits the bottom 146 of the slot 112. When the angle bar 132 hits the bottom 146 of the slot 112, the skull and/or vertebrae adjacent to the stopped vertebra continue moving. The misaligned joint between the vertebra that is stopped and the vertebra that continues moving are realigned as the vertebra is partially or completely sheared back into its proper position by this function (see FIGS. 3 and 4). The device 100 resists the elongate force on the neck because the superior (head up) force is resisted in the opposite direction. Each cervical vertebra, including the condyles of the skull, in need of repositioning may be treated by this method using the device 100 of the invention. It may be necessary for the practitioner to support the patient's head or neck on the side of the strap opposite the side of the misalignment under treatment, to prevent undesired action on normal joints. For example, for flexion, as shown in FIG. 10B, the point of intended treatment is between the C4 vertebra and the C5 vertebra, with the C5 vertebra to be sheared downward into alignment with C4. However, because of the weight of the head, there is some danger of the vertebra above the strap (C3) being sheared downward, as well. To prevent this, the practitioner may support the patient's head with one hand as he applies the additional force to the patient's body to activate the device.

Although it is possible for a patient to use this device alone, the patient would need proper training in the use of the device 100 before self-treatment could be recommended.

According to another aspect of the invention, the spinal adjustment device includes a reset lever configured to convert downward pressure on a handle of the lever into upward pressure against the lower surface of the upper plate in order to reset the device.

Figure 11:
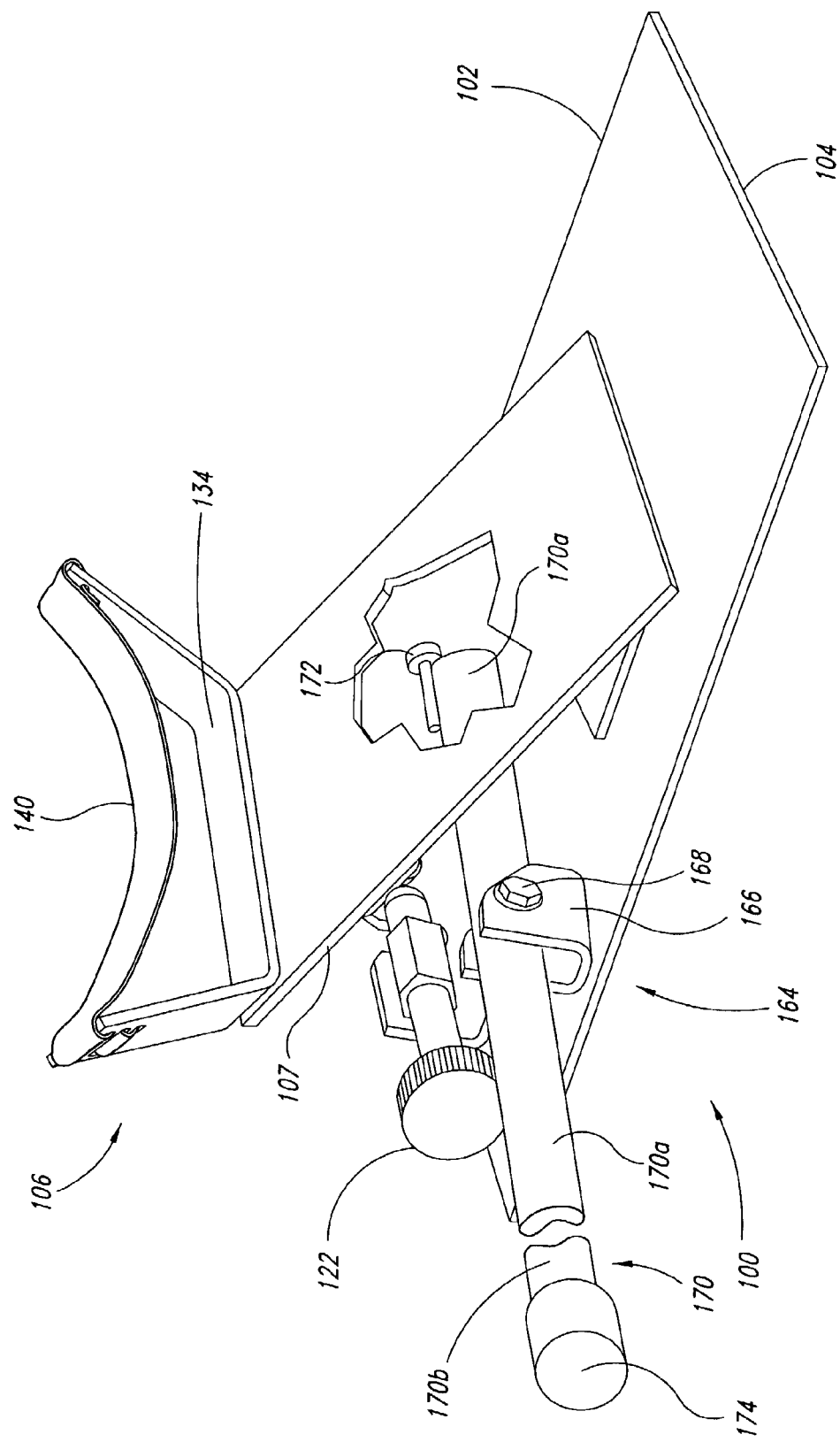
FIG. 11 is an isometric view of an alternative embodiment of the invention illustrating a reset lever.
Figure 12:
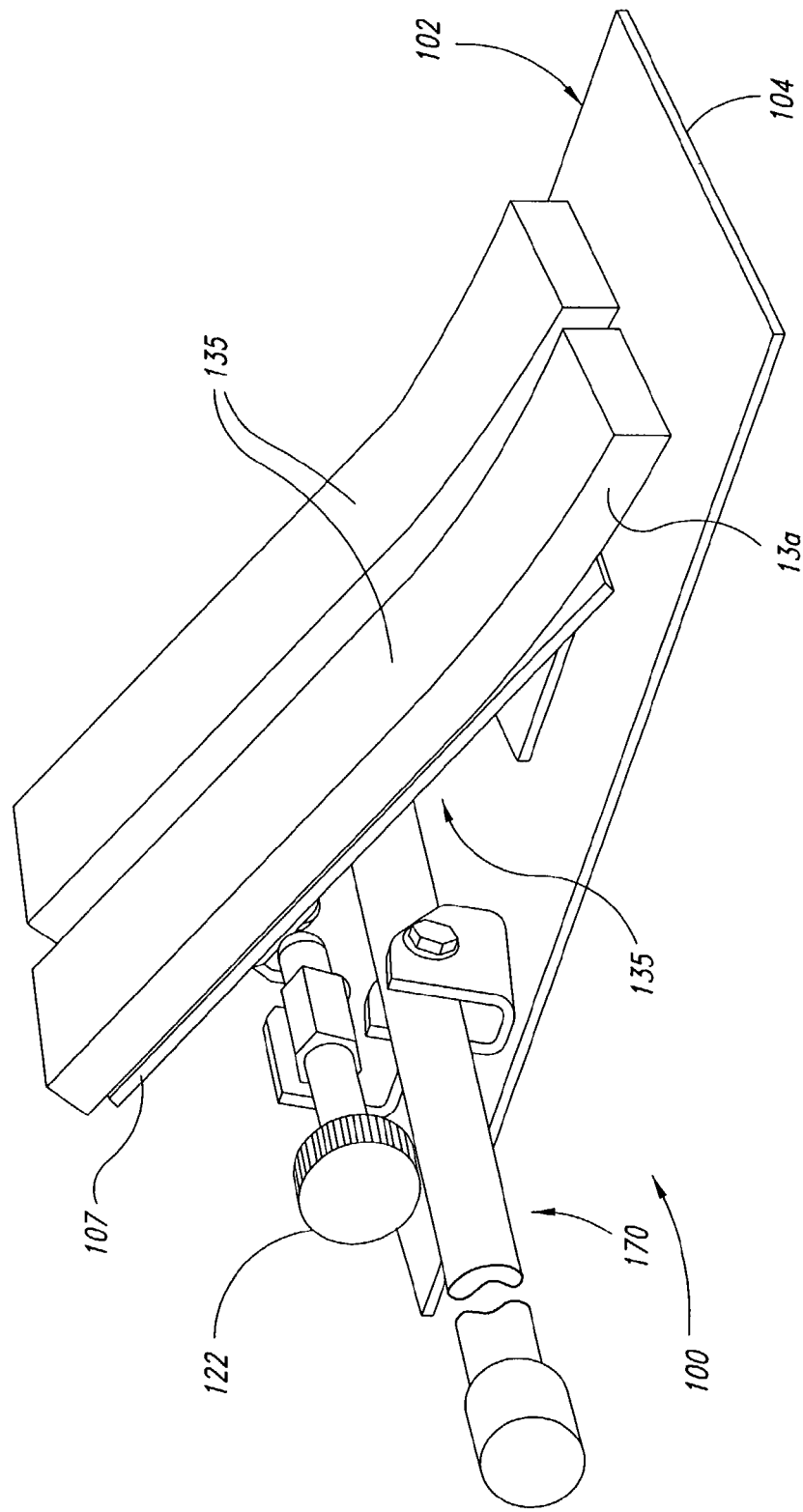
FIG. 12 is an isometric view of a spinal adjusting device configured for treating the vertebral column in accordance with another embodiment of the invention.

FIGS. 11 and 12 illustrate one example of such a reset lever. In this embodiment, the spinal adjustment device 100 includes a reset lever assembly 164 mounted thereon. The reset lever assembly 164 includes a mounting bracket 166 formed from a short length of 1"×1½" channel metal. The mounting bracket 166 is affixed to the base plate 104 at the right edge, as shown in FIG. 11. A bolt 168 passes through holes in the mounting bracket 166 and through holes in a reset lever 170, attaching the lever 170 to the bracket 166. Ideally, the lever 170 is formed from a length of rod or tubing, preferably ¾ inches in diameter and 8-14 inches long, which extends 3 to 4 inches inward from the bracket 166 to a point between the base plate 104 and the upper plate 107, and outward from the bracket 166 for a distance of 8-10 inches. The bolt acts as a pivot for the lever 170. The inner end 170*a* of the lever 170 further includes a reset bearing 172. The reset bearing 172 is preferably a roller bearing having a diameter of 1 inch and a thickness of ½ inch, and it is mounted on an upper portion of the inner end 170*a* of the lever 170 with a central axis parallel to the longitudinal axis of the reset lever 170 as illustrated in the cutaway view of FIG. 11. The outer end 170*b* of the reset lever 170 may include a handle or cover 174 to protect an operator's hand.

In operation, the lever 170 pivots on the bolt 168 on an axis parallel to the plane of the base plate 154 and perpendicular to a longitudinal axis of the lever 170. Up and down movement of the inner end 170*a* of the lever 170 is constrained by the upper surface of the base plate 154 in a first direction and by the lower surface of the upper plate 107 in the opposite direction. When the inner end 170*a* of the lever 170 is raised, the reset bearing 172 presses against the lower surface 124 of the upper plate 107.

The device 100 is reset or cocked by grasping the outer end 170*b* of the reset lever 170 and pressing it downward. The reset lever 170 pivots on the bolt 168, causing the inner end 170*a* of the lever 170 to press upward against the lower surface 124 of the upper plate 107. The force required to move the upper plate 107 into the cocked position is significantly less than that required to activate the device, inasmuch as, when in the uncocked position, the bearings 120 and 128 are separated by the leg 131 of the angle bar 132 and do not significantly resist upward movement of the leg 131. Because of the leverage provided by the position of the pivot point 168 on the lever 170, it is possible for the practitioner to reset the device 104 without removing the weight of the patient's head from the upper plate 107.

Figure 13:
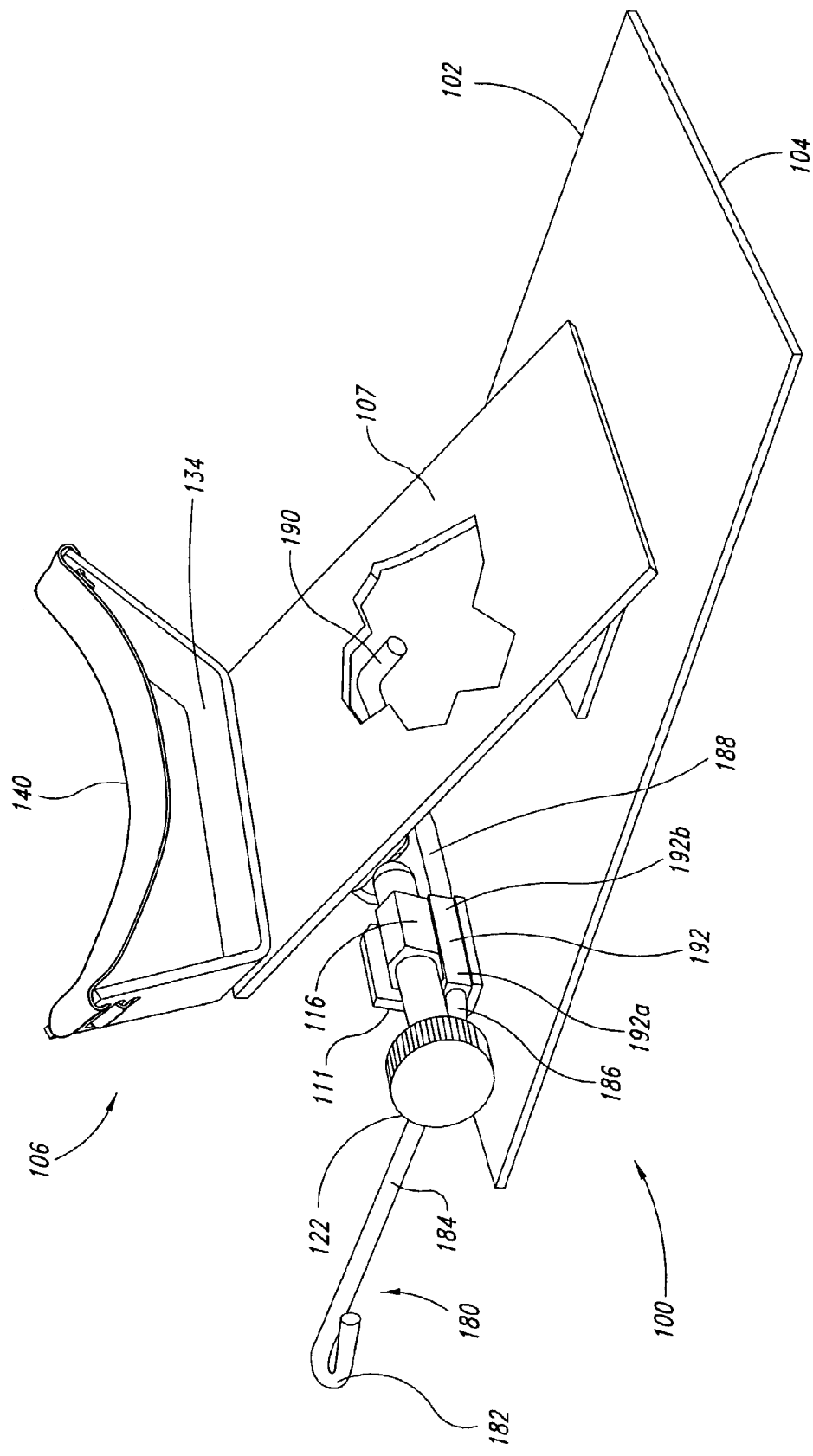
FIG. 13 is an isometric view of an embodiment of the invention illustrating a reset lever according to another embodiment of the invention.

FIG. 13 shows another embodiment of the reset lever, in which the reset lever 180 is formed from a single length of round bar. The bar may be mild steel having a diameter of about ⅜". The bar is bent to form a handle region 182, an arm region 184, a pivot region 186, a lifting region 188, and a reset foot 190. A pivot bracket 192 is welded or otherwise affixed to the upright angle plate 111 immediately beneath the coupling nut 116. The pivot region 186 of the lever 180 passes through the pivot bracket 192, which forms a fulcrum upon which the lever 180 rotates. From an outboard end 192*a* of the pivot bracket 192 the arm region 184 of the lever 180 curves in a direction away from the upper plate assembly 106 and terminates in the handle region 182. From an inboard end 192*b* of the pivot bracket 192 the lift region 188 of the lever 180 curves in a direction toward the upper plate assembly 106 and terminates in the reset foot 190, which is positioned between the upper and base plate assemblies 106, 102 in the approximate center of the upper plate 107. The handle and arm regions 180, 182 may be covered with a protective material to protect an operator's hands during operation, and the reset foot 190 may be covered with a material selected to reduce friction and wear at the point where the foot 190 contacts the lower surface of the upper plate 107.

In operation, the device is reset from an uncocked to a cocked position by exerting downward force on the handle region 182 of the lever 180. The lever pivots on the pivot bracket 192, causing the arm region 188 and the reset foot 190 to rise. The reset foot 190 exerts an upward force on the lower surface of the upper plate 107, causing the upper plate assembly 106 to rise to the cocked position. It will be understood that the ratio of upward force exerted by the reset foot 190 versus the downward force exerted on the handle region will be approximately proportionate to the length of the handle and arm regions 182, 184 versus the length of the lift region and reset foot 188, 190. Thus, a desired force multiplication ratio may be selected by selecting the respective lengths accordingly.

It is to be understood that while a preferred embodiment of the invention has been illustrated and described, various changes may be made therein without departing from the spirit and scope of the invention.

For example, the device components may be manufactured from steel, aluminum, or high-strength plastic, as appropriate. Common manufacturing methods may dictate changes in construction and assembly, such as replacing welds with bolts or rivets or vice-versa, etc. The dimensions may be varied according to specific applications, for example a device intended for use on children or small adults may be smaller, while a device intended for use on the lower spine may have variations in the dimensions or configuration. In addition, the invention may be used on other joints, such as a knee joint, where one part of the joint is held immobile and the other part of the joint can be moved with the device.

In an alternate embodiment of the device, indicated at 200 in FIG. 12, the bar 134 and strap 140 are absent. A resilient pad 135 is affixed to the upper surface of the upper plate 107 and preferably extends onto a portion of the base plate 104, as shown in FIG. 12. The resilient pad 135 forms a cushion between the patient's neck or back and the upper plate 107. The pad 135 may comprise two pads mounted to have a space between them to form a cradle for stabilizing a patient's spine on the upper plate. In such an embodiment, the pads 135 must be thick enough and positioned such that the patients back does not touch the upper plate 107.

For extension the device 200 is positioned under the patient with the rear edge 104*b* of the device directed toward the patient's feet, with the patient's head extending beyond the upper plate 107 and the forward edge 107*a* of the upper plate 107 under the vertebra below the vertebra in need of repositioning. For flexion the device 200 is positioned under the patient with the forward end 104*a* of the device directed toward the patient's feet, with the patient's body resting on the upper plate 107 and the forward edge 107*a* of the upper plate 107 under the vertebra above the vertebra in need of repositioning. In this orientation the practitioner may, as required for the comfort of the patient, raise the rearward end 104*b* from the patient table 142 to bring the upper surface of the upper plate 107 more closely parallel to the surface of the patient table 142. This may be accomplished by placing a spacer of the required thickness under the base plate. Such a configuration will also tend to bring the patient's body into a flexed position, which will simplify the adjustment.

For treatment of the lower joints and vertebrae of the spine, the device 200 is positioned with the forward edge 107a of the upper plate 107 under the joint to be treated, whether under the patient's back or pelvis, and activated as described above with reference to the neck vertebrae, for flexion or extension of the joint, as the case may be.

A further embodiment of the device, illustrated in FIG. 5, may include means for indicating the force required to overcome the resistance of the drop assembly 110, i.e., the threshold force. The indication means may comprise a graduated scale 182 on the base plate 104 and an index 184 on the thumbscrew 122. As the thumbscrew 122 is rotated, the index 184 moves over the scale 182, indicating the amount of compression exerted by the thumbscrew 122 on the spring 126, and thus the resistive pressure of the spring 126 on the bearings 120 and 128. A more accurate, albeit more complex indication means may include a device configured to directly measure and indicated tension on the bearings.

From the foregoing it will be appreciated that, although specific embodiments of the invention have been described herein for purposes of illustration, various modifications or combinations of the described embodiments may be made without deviating from the spirit and scope of the invention. Accordingly, the invention is not limited except as by the appended claims.

The embodiments of the invention in which an exclusive property or privilege is claimed are defined as follows:

1. A spinal adjusting device, comprising:
   a base plate;
   an upper plate assembly coupled to the base plate and movable from a first position to a second position relative to the base plate; and
   a drop assembly configured to resist force applied to the upper assembly of the spinal adjusting device such that the upper assembly remains in the first position while less than a threshold force is applied to the upper assembly, to release the upper plate assembly to drop from the first position to the second position when a force equal to or greater than the threshold force is applied to the upper plate assembly, and to stop the upper plate assembly at the second position and prevent further dropping of the upper plate assembly.

2. The spinal adjusting device of claim 1 wherein the threshold force is adjustable.

3. The spinal adjusting device of claim 1, further comprising a resilient pad on an upper surface of the upper plate assembly.

4. The spinal adjusting device of claim 1 wherein:
   the upper plate assembly is hinged at a first end to the base plate;
   the drop assembly is positioned under a second end of the upper plate assembly, opposite the first end.

5. The spinal adjusting device of claim 2 wherein the drop assembly includes calibration means for predictably establishing the threshold force.

6. The device of claim 1 wherein the upper plate assembly includes a plate portion having first and second ends, coupled to the base plate at the first end and configured to rotate around a first axis relative to the base plate, the upper plate assembly configured to receive a portion of a patient's weight thereon;
wherein the device comprises a lever having a central region and first and second ends, the lever rotatably coupled to the base plate at the central region and positioned such that the first end thereof is interposed between the base plate and the upper plate assembly and further such that force on the second end of the lever is transferred to the first end of the lever to urge the first end against an inner surface of the upper plate assembly to bias the upper plate assembly away from the base plate.

7. The device of claim 6 wherein:
   the lever comprises a metal rod positioned on the base plate such that the central region extends along a second axis substantially parallel to the first axis and is configured to rotate around the second axis;
   the rod having a first bend between the central region and the first end such that the first end extends into the position between the base plate the upper plate assembly; and
   the rod having a second bend between the central region and the fourth end such that the fourth end extends in a direction away from the third end.

8. The device of claim 1 wherein the drop assembly comprises:
   a first drop-assembly component coupled to the base plate and configured to receive a biasing pressure along a first axis that is parallel to the upper surface of the base plate;
   a second drop-assembly component coupled to the base plate and configured to move along the first axis relative to the base plate; and
   a biasing mechanism configured to apply a bias to the second drop-assembly component along the first axis, biasing the second component against the first component.

9. The device of claim 8 wherein the drop assembly further comprises a bias adjustment component configured to permit adjustment of the bias applied by the biasing mechanism.

10. The device of claim 9 wherein the drop assembly further comprises calibrating means for calibrating the biasing mechanism.

11. The device of claim 8, further comprising:
   a separator member coupled to the upper plate assembly and positioned such that, in an upper position, the separator member is configured to apply a separating force to the first and second drop-assembly components.

12. The device of claim 11 wherein a separating force required to interpose the separator member between the first and second drop-assembly components is directly related to a level of bias applied by the biasing mechanism.

13. A spinal adjusting device, comprising:
   a base plate;
   an upper plate assembly; and
   a coupling mechanism coupling the upper plate assembly to the base plate, the coupling mechanism including a drop assembly configured to release the upper plate assembly to drop from a first position to a second position when a predetermined amount of force is applied to the upper plate assembly, the drop assembly including;
   a projection affixed to the upper plate assembly and projecting toward the base plate; and
   first and second bearings affixed to the base plate, the first and second bearings urged together by a resilient force and positioned such that the projection bears against the first and second bearings, the resilient force selected to permit the bearings to be separated by the projection and allow the upper plate assembly to drop to the second position when the threshold force is applied to the upper plate assembly.

14. The spinal adjusting device of claim 13 wherein the resilient force is provided by a spring mounted to have a first end in contact with the first bearing and a second end in contact with a thumbscrew configured to enable adjustment of the resilient force.

15. A spinal adjusting device, comprising:

a base plate;

an upper plate assembly; and a coupling mechanism coupling the upper plate assembly to the base plate, the coupling mechanism including a drop assembly configured to release the upper plate assembly to drop from a first position to a second position when a predetermined amount of force is applied to the upper plate assembly; and a cradle that includes a flexible strap, the cradle coupled to the upper plate assembly on an upper surface thereof.

16. A spinal adjusting device, comprising:

a base plate;

an upper plate assembly; and a coupling mechanism coupling the upper plate assembly to the base plate, the coupling mechanism including a drop assembly configured to release the upper plate assembly to drop from a first position to a second position when a predetermined amount of force is applied to the upper plate assembly; and a reset lever configured to apply upward force on the upper plate assembly at a first end of the lever when downward force is applied to a second end of the lever, the upward force causing the upper plate assembly to move from the second position to the first position.

17. A spinal adjustment device, comprising:

means for supporting a patient;

means for holding the support means in a first position until a threshold force is exerted on the support means and to release the support means to drop to a second position when the threshold force is exerted on the support means; and means for stopping the support means at the second position.

18. The spinal adjustment device of claim 17 wherein the holding means comprises an adjusting means for varying a value of the threshold force.

19. The spinal adjustment device of claim 17 wherein:

the stopping means comprise a base plate;

the support means comprise an upper plate coupled at a first end to the base plate to angle upward from the first end and away from the base plate; and the holding means comprise an adjustable tension component configured such that the upper plate must overcome the tension of the component to drop to the base plate.

20. A spinal adjustment device, comprising:

means for supporting a first vertebra of a patient's spine in a first position while leaving a second adjacent vertebra unsupported;

means for releasing the patient's first and second vertebrae to drop when subjected to a threshold force; and means for stopping the drop of the first vertebra such that the second vertebra continues to drop.

21. A spinal adjusting device, comprising:

a base plate of the spinal adjusting device;

an upper plate assembly coupled to the base plate and movable between a cocked position and an uncocked position relative to the base plate; and a drop assembly configured to hold the upper plate assembly in the cocked position while a force applied to the upper plate assembly is less than a threshold force and further configured, when the force applied to the upper plate assembly is equal to or greater than the threshold force, to release the upper plate assembly to move from the cocked position toward the uncocked position and abruptly stop the movement of the upper plate assembly when it reaches the uncocked position.

* * * * *